(12) United States Patent
Kane et al.

(10) Patent No.: US 9,968,787 B2
(45) Date of Patent: May 15, 2018

(54) SPATIAL CONFIGURATION OF A MOTION SENSOR IN AN IMPLANTABLE MEDICAL DEVICE

(71) Applicant: CARDIAC PACEMAKERS, INC., St. Paul, MN (US)

(72) Inventors: Michael J. Kane, Roseville, MN (US); William J. Linder, Golden Valley, MN (US); Ron A. Balczewski, Bloomington, MN (US); Bin Mi, Plymouth, MN (US); John D. Hatlestad, Maplewood, MN (US); Paul Huelskamp, St. Paul, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days. days.

(21) Appl. No.: 15/243,550

(22) Filed: Aug. 22, 2016

(65) Prior Publication Data

US 2017/0056666 A1    Mar. 2, 2017

Related U.S. Application Data

(60) Provisional application No. 62/210,887, filed on Aug. 27, 2015.

(51) Int. Cl.
*A61N 1/365* (2006.01)
*A61N 1/372* (2006.01)
(Continued)

(52) U.S. Cl.
CPC ........ *A61N 1/36542* (2013.01); *A61B 5/0402* (2013.01); *A61B 5/1116* (2013.01);
(Continued)

(58) Field of Classification Search
None
See application file for complete search history.

(56) References Cited

U.S. PATENT DOCUMENTS

| | | |
|---|---|---|
| 3,835,864 A | 9/1974 | Rasor et al. |
| 3,943,936 A | 3/1976 | Rasor et al. |

(Continued)

FOREIGN PATENT DOCUMENTS

| | | |
|---|---|---|
| AU | 2008279789 B2 | 10/2011 |
| AU | 2008329620 B2 | 5/2014 |

(Continued)

OTHER PUBLICATIONS

US 8,886,318, 11/2014, Jacobson et al. (withdrawn)

(Continued)

*Primary Examiner* — Brian T Gedeon
(74) *Attorney, Agent, or Firm* — Seager, Tufte & Wickhem LLP

(57) ABSTRACT

Implantable devices having motion sensors. In some examples the a configuration is generated for the implantable device to use the motion sensor in an energy preserving mode in which one or more axis of detection of the motion sensor is disabled or ignored. In some examples the motion sensor outputs along multiple axes are analyzed to determine which axes best correspond to certain patient parameters including patient motion/activity and/or cardiac contractility. In other examples the output of the motion sensor is observed across patient movements or postures to develop conversion parameters to determine a patient standard frame of reference relative to outputs of the motion sensor of an implanted device.

19 Claims, 5 Drawing Sheets

(51) Int. Cl.
  *A61N 1/375* (2006.01)
  *A61N 1/37* (2006.01)
  *A61B 5/02* (2006.01)
  *A61B 5/0402* (2006.01)
  *A61B 5/11* (2006.01)
  *A61B 5/00* (2006.01)

(52) U.S. Cl.
  CPC ........ *A61B 5/1118* (2013.01); *A61N 1/36514* (2013.01); *A61N 1/36578* (2013.01); *A61N 1/36585* (2013.01); *A61N 1/3702* (2013.01); *A61N 1/3756* (2013.01); *A61N 1/37205* (2013.01); *A61N 1/37235* (2013.01); *A61B 5/02028* (2013.01); *A61B 5/6869* (2013.01)

(56) References Cited

U.S. PATENT DOCUMENTS

| | | | |
|---|---|---|---|
| 4,142,530 | A | 3/1979 | Wittkampf |
| 4,151,513 | A | 4/1979 | Menken et al. |
| 4,157,720 | A | 6/1979 | Greatbatch |
| RE30,366 | E | 8/1980 | Rasor et al. |
| 4,250,884 | A | 2/1981 | Hartlaub et al. |
| 4,256,115 | A | 3/1981 | Bilitch |
| 4,263,919 | A | 4/1981 | Levin |
| 4,310,000 | A | 1/1982 | Lindemans |
| 4,312,354 | A | 1/1982 | Walters |
| 4,323,081 | A | 4/1982 | Wiebusch |
| 4,357,946 | A | 11/1982 | Dutcher et al. |
| 4,365,639 | A | 12/1982 | Goldreyer |
| 4,440,173 | A | 4/1984 | Hudziak et al. |
| 4,476,868 | A | 10/1984 | Thompson |
| 4,522,208 | A | 6/1985 | Buffet |
| 4,556,063 | A | 12/1985 | Thompson et al. |
| 4,562,841 | A | 1/1986 | Brockway et al. |
| 4,593,702 | A | 6/1986 | Kepski et al. |
| 4,593,955 | A | 6/1986 | Leiber |
| 4,630,611 | A | 12/1986 | King |
| 4,635,639 | A | 1/1987 | Hakala et al. |
| 4,674,508 | A | 6/1987 | DeCote |
| 4,712,554 | A | 12/1987 | Garson |
| 4,729,376 | A | 3/1988 | DeCote |
| 4,754,753 | A | 7/1988 | King |
| 4,759,366 | A | 7/1988 | Callaghan |
| 4,787,389 | A | 11/1988 | Tarjan |
| 4,793,353 | A | 12/1988 | Borkan |
| 4,819,662 | A | 4/1989 | Heil et al. |
| 4,858,610 | A | 8/1989 | Callaghan et al. |
| 4,886,064 | A | 12/1989 | Strandberg |
| 4,928,688 | A | 5/1990 | Mower |
| 4,967,746 | A | 11/1990 | Vandegriff |
| 4,987,897 | A | 1/1991 | Funke |
| 4,989,602 | A | 2/1991 | Sholder et al. |
| 5,012,806 | A | 5/1991 | De Bellis |
| 5,036,849 | A | 8/1991 | Hauck et al. |
| 5,058,581 | A | 10/1991 | Silvian |
| 5,078,134 | A | 1/1992 | Heilman et al. |
| 5,109,845 | A | 5/1992 | Yuuchi et al. |
| 5,113,859 | A | 5/1992 | Funke |
| 5,117,824 | A | 6/1992 | Keimel et al. |
| 5,127,401 | A | 7/1992 | Grevious et al. |
| 5,133,353 | A | 7/1992 | Hauser |
| 5,144,950 | A | 9/1992 | Stoop et al. |
| 5,170,784 | A | 12/1992 | Ramon et al. |
| 5,179,945 | A | 1/1993 | Van Hofwegen et al. |
| 5,193,539 | A | 3/1993 | Schulman et al. |
| 5,193,540 | A | 3/1993 | Schulman et al. |
| 5,241,961 | A | 9/1993 | Henry |
| 5,243,977 | A | 9/1993 | Trabucco et al. |
| 5,269,326 | A | 12/1993 | Verrier |
| 5,284,136 | A | 2/1994 | Hauck et al. |
| 5,300,107 | A | 4/1994 | Stokes et al. |
| 5,301,677 | A | 4/1994 | Hsung |
| 5,312,439 | A | 5/1994 | Loeb |
| 5,313,953 | A | 5/1994 | Yomtov et al. |
| 5,314,459 | A | 5/1994 | Swanson et al. |
| 5,318,596 | A | 6/1994 | Barreras |
| 5,318,597 | A | 6/1994 | Hauck et al. |
| 5,324,316 | A | 6/1994 | Schulman et al. |
| 5,331,966 | A | 7/1994 | Bennett et al. |
| 5,334,222 | A | 8/1994 | Salo et al. |
| 5,342,408 | A | 8/1994 | Decoriolis et al. |
| 5,372,606 | A | 12/1994 | Lang et al. |
| 5,376,106 | A | 12/1994 | Stahmann et al. |
| 5,383,915 | A | 1/1995 | Adams |
| 5,388,578 | A | 2/1995 | Yomtov et al. |
| 5,404,877 | A | 4/1995 | Nolan et al. |
| 5,405,367 | A | 4/1995 | Schulman et al. |
| 5,411,031 | A | 5/1995 | Yomtov |
| 5,411,525 | A | 5/1995 | Swanson et al. |
| 5,411,535 | A | 5/1995 | Fujii et al. |
| 5,456,691 | A | 10/1995 | Snell |
| 5,466,246 | A | 11/1995 | Silvian |
| 5,468,254 | A | 11/1995 | Hahn et al. |
| 5,514,162 | A * | 5/1996 | Bornzin ............ A61N 1/36542 607/19 |
| 5,522,866 | A | 6/1996 | Fernald |
| 5,540,727 | A | 7/1996 | Tockman et al. |
| 5,545,186 | A | 8/1996 | Olson et al. |
| 5,545,202 | A | 8/1996 | Dahl et al. |
| 5,549,650 | A * | 8/1996 | Bornzin ............ A61N 1/36542 607/24 |
| 5,591,214 | A | 1/1997 | Lu |
| 5,620,466 | A | 4/1997 | Haefner et al. |
| 5,634,938 | A | 6/1997 | Swanson et al. |
| 5,662,688 | A | 9/1997 | Haefner et al. |
| 5,674,259 | A | 10/1997 | Gray |
| 5,683,426 | A | 11/1997 | Greenhut et al. |
| 5,683,432 | A | 11/1997 | Goedeke et al. |
| 5,720,770 | A | 2/1998 | Nappholz et al. |
| 5,728,154 | A | 3/1998 | Crossett et al. |
| 5,741,314 | A | 4/1998 | Daly et al. |
| 5,741,315 | A | 4/1998 | Lee et al. |
| 5,752,976 | A | 5/1998 | Duffin et al. |
| 5,752,977 | A | 5/1998 | Grevious et al. |
| 5,755,736 | A | 5/1998 | Gillberg et al. |
| 5,759,199 | A | 6/1998 | Snell et al. |
| 5,774,501 | A | 6/1998 | Halpern et al. |
| 5,792,202 | A | 8/1998 | Rueter |
| 5,792,203 | A | 8/1998 | Schroeppel |
| 5,792,205 | A | 8/1998 | Alt et al. |
| 5,792,208 | A | 8/1998 | Gray |
| 5,814,089 | A | 9/1998 | Stokes et al. |
| 5,827,216 | A | 10/1998 | Igo et al. |
| 5,836,985 | A | 11/1998 | Goyal et al. |
| 5,836,987 | A | 11/1998 | Baumann et al. |
| 5,842,977 | A | 12/1998 | Lesho et al. |
| 5,855,593 | A | 1/1999 | Olson et al. |
| 5,873,894 | A | 2/1999 | Vandegriff et al. |
| 5,891,184 | A | 4/1999 | Lee et al. |
| 5,897,586 | A | 4/1999 | Molina |
| 5,899,876 | A | 5/1999 | Flower |
| 5,899,928 | A | 5/1999 | Sholder et al. |
| 5,919,214 | A | 7/1999 | Ciciarelli et al. |
| 5,935,078 | A | 8/1999 | Feierbach |
| 5,941,906 | A | 8/1999 | Barreras et al. |
| 5,954,757 | A | 9/1999 | Gray |
| 5,978,713 | A | 11/1999 | Prutchi et al. |
| 5,991,660 | A | 11/1999 | Goyal |
| 5,999,848 | A | 12/1999 | Gord et al. |
| 5,999,857 | A | 12/1999 | Weijand et al. |
| 6,026,320 | A | 2/2000 | Carlson et al. |
| 6,044,298 | A | 3/2000 | Salo et al. |
| 6,044,300 | A | 3/2000 | Gray |
| 6,055,454 | A | 4/2000 | Heemels |
| 6,073,050 | A | 6/2000 | Griffith |
| 6,076,016 | A | 6/2000 | Feierbach |
| 6,080,187 | A | 6/2000 | Alt et al. |
| 6,083,248 | A | 7/2000 | Thompson |
| 6,106,551 | A | 8/2000 | Crossett et al. |
| 6,115,636 | A | 9/2000 | Ryan |
| 6,141,581 | A | 10/2000 | Olson et al. |
| 6,141,588 | A | 10/2000 | Cox et al. |
| 6,141,592 | A | 10/2000 | Pauly |

(56) References Cited

U.S. PATENT DOCUMENTS

| | | |
|---|---|---|
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,190,324 B1 * | 2/2001 | Kieval .................. A61B 5/024 600/483 |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,298,271 B1 | 10/2001 | Weijand |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,110,824 B2 | 9/2006 | Amundson et al. |
| 7,120,504 B2 | 10/2006 | Osypka |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,790 B2 | 4/2007 | Thompson et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |

(56) References Cited

U.S. PATENT DOCUMENTS

| | | | |
|---|---|---|---|
| 7,384,403 B2 | 6/2008 | Sherman | |
| 7,386,342 B1 | 6/2008 | Falkenberg et al. | |
| 7,392,090 B2 | 6/2008 | Sweeney et al. | |
| 7,406,105 B2 | 7/2008 | DelMain et al. | |
| 7,406,349 B2 | 7/2008 | Seeberger et al. | |
| 7,410,497 B2 | 8/2008 | Hastings et al. | |
| 7,425,200 B2 | 9/2008 | Brockway et al. | |
| 7,433,739 B1 | 10/2008 | Salys et al. | |
| 7,496,409 B2 | 2/2009 | Greenhut et al. | |
| 7,496,410 B2 | 2/2009 | Heil | |
| 7,502,652 B2 | 3/2009 | Gaunt et al. | |
| 7,512,448 B2 | 3/2009 | Malick et al. | |
| 7,515,969 B2 | 4/2009 | Tockman et al. | |
| 7,526,342 B2 | 4/2009 | Chin et al. | |
| 7,529,589 B2 | 5/2009 | Williams et al. | |
| 7,532,933 B2 | 5/2009 | Hastings et al. | |
| 7,536,222 B2 | 5/2009 | Bardy et al. | |
| 7,539,541 B2 | 5/2009 | Quiles et al. | |
| 7,544,197 B2 | 6/2009 | Kelsch et al. | |
| 7,558,631 B2 | 7/2009 | Cowan et al. | |
| 7,565,195 B1 | 7/2009 | Kroll et al. | |
| 7,584,002 B2 | 9/2009 | Burnes et al. | |
| 7,590,455 B2 | 9/2009 | Heruth et al. | |
| 7,606,621 B2 | 10/2009 | Brisken et al. | |
| 7,610,088 B2 | 10/2009 | Chinchoy | |
| 7,610,092 B2 | 10/2009 | Cowan et al. | |
| 7,610,099 B2 | 10/2009 | Almendinger et al. | |
| 7,610,104 B2 | 10/2009 | Kaplan et al. | |
| 7,616,991 B2 | 11/2009 | Mann et al. | |
| 7,617,001 B2 | 11/2009 | Penner et al. | |
| 7,617,007 B2 | 11/2009 | Williams et al. | |
| 7,630,767 B1 | 12/2009 | Poore et al. | |
| 7,634,313 B1 | 12/2009 | Kroll et al. | |
| 7,637,867 B2 | 12/2009 | Zdeblick | |
| 7,640,060 B2 | 12/2009 | Zdeblick | |
| 7,647,109 B2 | 1/2010 | Hastings et al. | |
| 7,650,186 B2 | 1/2010 | Hastings et al. | |
| 7,657,311 B2 | 2/2010 | Bardy et al. | |
| 7,668,596 B2 | 2/2010 | Von Arx et al. | |
| 7,691,047 B2 | 4/2010 | Ferrari | |
| 7,702,392 B2 | 4/2010 | Echt et al. | |
| 7,713,194 B2 | 5/2010 | Zdeblick | |
| 7,713,195 B2 | 5/2010 | Zdeblick | |
| 7,715,915 B1 * | 5/2010 | Ryu | A61N 1/36114 607/14 |
| 7,729,783 B2 | 6/2010 | Michels et al. | |
| 7,734,333 B2 | 6/2010 | Ghanem et al. | |
| 7,734,343 B2 | 6/2010 | Ransbury et al. | |
| 7,738,958 B2 | 6/2010 | Zdeblick et al. | |
| 7,738,964 B2 | 6/2010 | Von Arx et al. | |
| 7,742,812 B2 | 6/2010 | Ghanem et al. | |
| 7,742,816 B2 | 6/2010 | Masoud et al. | |
| 7,742,822 B2 | 6/2010 | Masoud et al. | |
| 7,743,151 B2 | 6/2010 | Vallapureddy et al. | |
| 7,747,335 B2 | 6/2010 | Williams | |
| 7,751,881 B2 | 7/2010 | Cowan et al. | |
| 7,758,521 B2 | 7/2010 | Morris et al. | |
| 7,761,150 B2 | 7/2010 | Ghanem et al. | |
| 7,761,164 B2 | 7/2010 | Verhoef et al. | |
| 7,765,001 B2 | 7/2010 | Echt et al. | |
| 7,769,452 B2 | 8/2010 | Ghanem et al. | |
| 7,792,588 B2 | 9/2010 | Harding | |
| 7,797,059 B1 | 9/2010 | Bomzin et al. | |
| 7,801,596 B2 | 9/2010 | Fischell et al. | |
| 7,809,438 B2 | 10/2010 | Echt et al. | |
| 7,840,281 B2 | 11/2010 | Kveen et al. | |
| 7,844,348 B2 | 11/2010 | Swoyer et al. | |
| 7,846,088 B2 | 12/2010 | Ness | |
| 7,848,815 B2 | 12/2010 | Brisken et al. | |
| 7,848,823 B2 | 12/2010 | Drasler et al. | |
| 7,860,455 B2 | 12/2010 | Fukumoto et al. | |
| 7,871,433 B2 | 1/2011 | Lattouf | |
| 7,877,136 B1 | 1/2011 | Moffitt et al. | |
| 7,877,142 B2 | 1/2011 | Moaddeb et al. | |
| 7,881,798 B2 | 2/2011 | Miesel et al. | |
| 7,881,810 B1 | 2/2011 | Chitre et al. | |
| 7,890,173 B2 | 2/2011 | Brisken et al. | |
| 7,890,181 B2 | 2/2011 | Denzene et al. | |
| 7,890,192 B1 | 2/2011 | Kelsch et al. | |
| 7,894,894 B2 | 2/2011 | Stadler et al. | |
| 7,894,907 B2 | 2/2011 | Cowan et al. | |
| 7,894,910 B2 | 2/2011 | Cowan et al. | |
| 7,894,915 B1 | 2/2011 | Chitre et al. | |
| 7,899,537 B1 | 3/2011 | Kroll et al. | |
| 7,899,541 B2 | 3/2011 | Cowan et al. | |
| 7,899,542 B2 | 3/2011 | Cowan et al. | |
| 7,899,554 B2 | 3/2011 | Williams et al. | |
| 7,901,360 B1 | 3/2011 | Yang et al. | |
| 7,904,170 B2 | 3/2011 | Harding | |
| 7,907,993 B2 | 3/2011 | Ghanem et al. | |
| 7,920,928 B1 | 4/2011 | Yang et al. | |
| 7,925,343 B1 | 4/2011 | Min et al. | |
| 7,930,040 B1 | 4/2011 | Kelsch et al. | |
| 7,937,135 B2 | 5/2011 | Ghanem et al. | |
| 7,937,148 B2 * | 5/2011 | Jacobson | A61N 1/3708 600/373 |
| 7,937,161 B2 | 5/2011 | Hastings et al. | |
| 7,941,214 B2 | 5/2011 | Kleckner et al. | |
| 7,945,333 B2 | 5/2011 | Jacobson | |
| 7,946,997 B2 | 5/2011 | Hübinette | |
| 7,949,404 B2 | 5/2011 | Hill | |
| 7,949,405 B2 | 5/2011 | Feher | |
| 7,953,493 B2 | 5/2011 | Fowler et al. | |
| 7,962,202 B2 | 6/2011 | Bhunia | |
| 7,974,702 B1 | 7/2011 | Fain et al. | |
| 7,979,136 B2 | 7/2011 | Young et al. | |
| 7,983,753 B2 | 7/2011 | Severin | |
| 3,010,209 A1 | 8/2011 | Jacobson | |
| 7,991,467 B2 | 8/2011 | Markowitz et al. | |
| 7,991,471 B2 | 8/2011 | Ghanem et al. | |
| 7,996,087 B2 | 8/2011 | Cowan et al. | |
| 8,000,791 B2 | 8/2011 | Sunagawa et al. | |
| 8,000,807 B2 | 8/2011 | Morris et al. | |
| 8,001,975 B2 | 8/2011 | DiSilvestro et al. | |
| 8,002,700 B2 | 8/2011 | Ferek-Petric et al. | |
| 8,019,419 B1 | 9/2011 | Panescu et al. | |
| 8,019,434 B2 | 9/2011 | Quiles et al. | |
| 8,027,727 B2 | 9/2011 | Freeberg | |
| 8,027,729 B2 | 9/2011 | Sunagawa et al. | |
| 8,032,219 B2 | 10/2011 | Neumann et al. | |
| 8,036,743 B2 | 10/2011 | Savage et al. | |
| 8,046,079 B2 | 10/2011 | Bange et al. | |
| 8,046,080 B2 | 10/2011 | Von Arx et al. | |
| 8,050,297 B2 | 11/2011 | Delmain et al. | |
| 8,050,759 B2 | 11/2011 | Stegemann et al. | |
| 8,050,774 B2 | 11/2011 | Kveen et al. | |
| 8,055,345 B2 | 11/2011 | Li et al. | |
| 8,055,350 B2 | 11/2011 | Roberts | |
| 8,060,212 B1 | 11/2011 | Rios et al. | |
| 8,065,018 B2 | 11/2011 | Haubrich et al. | |
| 8,073,542 B2 | 12/2011 | Doerr | |
| 8,078,278 B2 | 12/2011 | Penner | |
| 8,078,283 B2 | 12/2011 | Cowan et al. | |
| 8,095,123 B2 | 1/2012 | Gray | |
| 8,102,789 B2 | 1/2012 | Rosar et al. | |
| 8,103,359 B2 | 1/2012 | Reddy | |
| 8,103,361 B2 | 1/2012 | Moser | |
| 8,112,148 B2 | 2/2012 | Giftakis et al. | |
| 8,114,021 B2 | 2/2012 | Robertson et al. | |
| 8,121,680 B2 | 2/2012 | Falkenberg et al. | |
| 8,123,684 B2 | 2/2012 | Zdeblick | |
| 8,126,545 B2 | 2/2012 | Flach et al. | |
| 8,131,334 B2 | 3/2012 | Lu et al. | |
| 8,140,161 B2 | 3/2012 | Willerton et al. | |
| 8,150,521 B2 | 4/2012 | Crowley et al. | |
| 8,160,672 B2 | 4/2012 | Kim et al. | |
| 8,160,702 B2 | 4/2012 | Mann et al. | |
| 8,160,704 B2 | 4/2012 | Freeberg | |
| 8,165,694 B2 | 4/2012 | Carbanaru et al. | |
| 8,175,715 B1 | 5/2012 | Cox | |
| 8,180,451 B2 | 5/2012 | Hickman et al. | |
| 8,185,213 B2 | 5/2012 | Kveen et al. | |
| 8,187,161 B2 | 5/2012 | Li et al. | |
| 8,204,595 B2 | 6/2012 | Pianca et al. | |

(56) References Cited

U.S. PATENT DOCUMENTS

| | | |
|---|---|---|
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,233,985 B2 | 7/2012 | Bulkes et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,527,068 B2 | 9/2013 | Ostroff |
| 8,532,790 B2 | 9/2013 | Griswold |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,878 B2 | 10/2013 | Allavatam et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,773 B2 | 5/2014 | Willis et al. |
| 8,738,147 B2 | 5/2014 | Hastings et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,500 B2 | 12/2014 | Smith et al. |
| 8,903,513 B2 | 12/2014 | Ollivier |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |

(56) References Cited

U.S. PATENT DOCUMENTS

| | | |
|---|---|---|
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0041866 A1 | 3/2003 | Linberg et al. |
| 2003/0088278 A1 | 5/2003 | Bardy et al. |
| 2003/0097153 A1 | 5/2003 | Bardy et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0178586 A1 | 8/2006 | Dobak |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |

(56) References Cited

U.S. PATENT DOCUMENTS

| | | |
|---|---|---|
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |

(56) References Cited

U.S. PATENT DOCUMENTS

| | | |
|---|---|---|
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bomzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0257324 A1 | 9/2014 | Fain |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0173655 A1 | 6/2015 | Demmer |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishier et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |

OTHER PUBLICATIONS

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration, dated Jan. 29, 2016, 15 pages.

(56) References Cited

OTHER PUBLICATIONS

Spickler et al., "Totally Self-Contained Intracardiac Pacemaker," Journal of Electrocardiology, vol. 3(3&4): 324-331, 1970.
"Instructions for Use System 1, Leadless Cardiac Pacemaker (LCP) and Delivery Catheter," Nanostim Leadless Pacemakers, pp. 1-28, 2013.
International Search Report and Written Opinion dated Feb. 18, 2017 for International Application No. PCT/US2016/048360.

* cited by examiner

SPATIAL CONFIGURATION OF A MOTION SENSOR IN AN IMPLANTABLE MEDICAL DEVICE

CROSS REFERENCE TO RELATED APPLICATIONS

The present application claims the benefit of and priority to U.S. Provisional Patent Application Ser. No. 62/210,887, filed on Aug. 27, 2015, the disclosure of which is incorporated herein by reference.

TECHNICAL FIELD

The present disclosure generally relates to systems, devices, and methods for treating medical conditions using an implantable device, and more particularly, to systems, devices, and methods which include or use a motion sensor to detect a patient's level of activity.

BACKGROUND

Pacing instruments can be used to treat patients suffering from various heart conditions that result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) have been implanted in a patient's body. Such devices may monitor and provide electrical stimulation to the heart to help the heart operate in a more normal, efficient and/or safe manner. In some cases, a patient may have multiple implanted devices.

Motion detectors have been used in some pacemakers and other implantable devices to obtain a measure of the activity level of the patient. For example, rate adaptive cardiac pacemakers may adjust the rate at which the patient's heart is paced up or down in response to detected motion of the patient. By so doing, the pacemaker is able to adapt to the activity level of the patient, allowing a more active lifestyle than could be achieved without rate adaptive pacing. New and alternative approaches to the use of motion sensors are desired.

Overview

The present inventors have recognized that a problem to be solved includes the manner in which an implantable device uses a motion sensor having multiple axes. In some examples a configuration is generated for the implantable device to use the motion sensor in an energy preserving mode in which one or more axes of detection of the motion sensor is disabled or ignored. In some examples the motion sensor outputs along multiple axes are analyzed to determine which axes best correspond to certain patient parameters including patient motion/activity and/or cardiac contractility, to simplify and possibly enhance the accuracy of data analysis. In other examples the output of the motion sensor is observed across patient movements or postures to develop conversion parameters to determine a patient standard frame of reference relative to outputs of the motion sensor of an implanted device.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This disclosure describes systems, devices, and methods for delivering electrical stimulation to a heart in a rate adaptive manner. Healthy people's bodies generally adjust the rate at which their hearts beat in response to higher or lower metabolic needs, for example during exercise or in response to various external stimuli. However, some people develop diseases or conditions which affect their bodies' abilities to cause their hearts to contract in an effective manner. Devices in accordance with the present disclosure may be implanted in such people. In some instances, the implanted devices may deliver electrical stimulation on an on-going basis and adjust the rate of delivered electrical stimulation in accordance with sensed physiological parameters indicative of increased metabolic needs.

Figure 1:
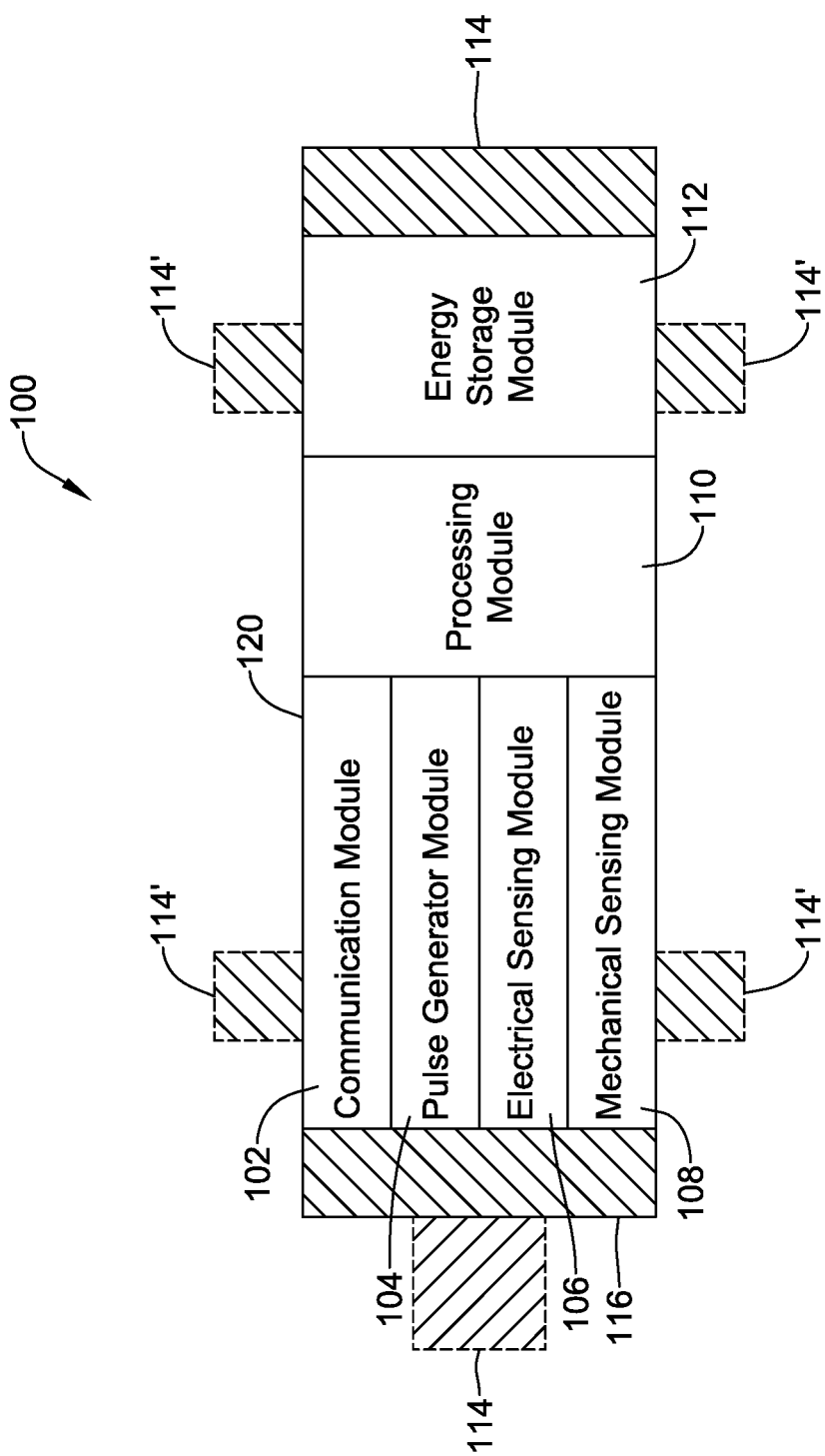
FIG. 1 is a schematic block diagram of an illustrative implantable device.

FIG. 1 is similar to FIG. 1 of commonly assigned and U.S. Provisional Patent Application 62/128,340, the disclosure of which is incorporated herein by reference as showing and describing numerous additional details which may be included in the methods, systems and devices discussed herein.

More specifically, FIG. 1 is a conceptual schematic block diagram of an exemplary leadless cardiac pacemaker (LCP) that may be implanted on the heart or within a chamber of the heart and may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 1, LCP 100 may be a compact device with all components housed within LCP 100 or directly on housing 120. In some instances, LCP 100 may include communication module 102, pulse generator module 104, electrical sensing module 106, mechanical sensing module 108, processing module 110, energy storage module 112, and electrodes 114. In some examples (not shown), an optional lead or tether may be attached to an implantable device similar to LCP 100 to provide an additional electrode, extended antenna functionality, to couple to a second such implantable device, or to prevent migration.

As depicted in FIG. 1, LCP 100 may include electrodes 114, which can be secured relative to housing 120 and electrically exposed to tissue and/or blood surrounding LCP 100. Electrodes 114 may generally conduct electrical signals to and from LCP 100 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by the cardiac electrogram (EGM), if observed on or in the heart, or the electrocardiogram (ECG), if observed at some distance from the heart.

Electrodes 114 may include one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In embodiments where electrodes 114 are secured directly to housing 120, an insulating material may electrically isolate the electrodes 114 from adjacent electrodes, housing 120, and/or other parts of LCP 100. In some instances, some or all of electrodes 114 may be spaced from housing 120 and connected to housing 120 and/or other components of LCP 100 through connecting wires. In such instances, the electrodes 114 may be placed on a tail (not shown) that extends out away from the housing 120. As shown in FIG. 1, in some embodiments, LCP 100 may include electrodes 114'. Electrodes 114' may be in addition to electrodes 114, or may replace one or more of electrodes 114. Electrodes 114' may be similar to electrodes 114 except that electrodes 114' are disposed on the sides of LCP 100. In some cases, electrodes 114' may increase the number of electrodes by which LCP 100 may deliver communication signals and/or electrical stimulation pulses, and/or may sense intrinsic cardiac electrical signals, communication signals, and/or electrical stimulation pulses.

Electrodes 114 and/or 114' may assume any of a variety of sizes and/or shapes, and may be spaced at any of a variety of spacings. For example, electrodes 114 may have an outer diameter of two to twenty millimeters (mm). In other embodiments, electrodes 114 and/or 114' may have a diameter of two, three, five, seven millimeters (mm), or any other suitable diameter, dimension and/or shape. Example lengths for electrodes 114 and/or 114' may include, for example, one, three, five, ten millimeters (mm), or any other suitable length. As used herein, the length is a dimension of electrodes 114 and/or 114' that extends away from the outer surface of the housing 120. In some instances, at least some of electrodes 114 and/or 114' may be spaced from one another by a distance of twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In the embodiment shown, communication module 102 may be electrically coupled to electrodes 114 and/or 114' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. Communication module 102 may additionally be configured to sense for communication signals delivered by other devices, which may be located external or internal to the patient's body.

Communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, LCP 100 may use communication signals to communicate raw information, processed information, messages and/or commands, and/or other data. Raw information may include information such as sensed electrical signals (e.g. a sensed EGM), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

In at least some embodiments, communication module 102 (or LCP 100) may further include switching circuitry to selectively connect one or more of electrodes 114 and/or 114' to communication module 102 in order to select which electrodes 114 and/or 114' that communication module 102 delivers communication pulses. It is contemplated that communication module 102 may be communicating with other devices via conducted signals, radio frequency (RF) signals, optical signals, acoustic signals, inductive coupling, and/or any other suitable communication methodology. Where communication module 102 generates electrical communication signals, communication module 102 may include one or more capacitor elements and/or other charge storage devices to aid in generating and delivering communication signals. In the embodiment shown, communication module 102 may use energy stored in energy storage module 112 to generate the communication signals. In at least some examples, communication module 102 may include a switching circuit that is connected to energy storage module 112 and, with the switching circuitry, may connect energy storage module 112 to one or more of electrodes 114/114' to generate the communication signals.

As shown in FIG. 1, a pulse generator module 104 may be electrically connected to one or more of electrodes 114 and/or 114'. Pulse generator module 104 may be configured to generate electrical stimulation pulses and deliver the electrical stimulation pulses to tissues of a patient via one or more of the electrodes 114 and/or 114' to provide one or more electrical stimulation therapies such as bradycardia pacing, ATP, CRT, cardioversion, or defibrillation.

The LCP 100 may vary the rate at which pulse generator 104 generates the electrical stimulation pulses, for example in rate adaptive pacing. These are just some examples. When used to treat other ailments, the pulse generator module 104 may generate electrical stimulation pulses suitable for neurostimulation or neuromodulation therapy or the like.

Pulse generator module 104 may include one or more capacitor elements and/or other charge storage devices to aid in generating and delivering appropriate electrical stimulation pulses. In the embodiment shown, pulse generator module 104 may use energy stored in energy storage module 112 to generate the electrical stimulation pulses. In some examples, pulse generator module 104 may include a switching circuit that is connected to energy storage module 112 and may connect energy storage module 112 to one or more of electrodes 114/114' to generate electrical stimulation pulses.

Pulse generator module 104 may include the capability to modify the electrical stimulation pulses, such as by adjusting the pulse width and/or amplitude of the electrical stimulation pulses. When pacing the heart, this may help tailor the electrical stimulation pulses to capture the heart a particular patient, sometimes with reduced battery usage. For neurostimulation therapy, adjusting the pulse width and/or amplitude may help tailor the therapy for a particular application and/or help make the therapy more effective for a particular patient.

In some embodiments, LCP 100 may include an electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114' via a sensor amplifier or the like. In some embodiments, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals.

Mechanical sensing module 108 may include, or be electrically connected to, various sensors, such as accelerometers, blood pressure sensors, heart sound sensors, piezoelectric sensors, blood-oxygen sensors, and/or other sensors which measure one or more physiological parameters of the heart and/or patient. Mechanical sensing module 108 may gather signals from the sensors indicative of the various physiological parameters. Both electrical sensing module 106 and mechanical sensing module 108 may be connected to processing module 110 and may provide signals representative of the sensed cardiac electrical signals and/or physiological signals to processing module 110. Although described with respect to FIG. 1 as separate sensing modules, in some embodiments, electrical sensing module 106 and mechanical sensing module 108 may be combined into a single module. In at least some examples, LCP 100 may only include one of electrical sensing module 106 and mechanical sensing module 108. In some cases, any combination of the processing module 110, electrical sensing module 106, mechanical sensing module 108, communication module 102, pulse generator module 104 and/or energy storage module may be considered a controller of the LCP 100.

The mechanical sensing module may include, for example, a micro-electro-mechanical system (MEMS) based motion sensor. This may include a 1, 2 or 3 dimensional motion sensor and may take any of numerous forms known in the art. Some examples may include a micromachine size vibrating element that varies an electrical parameter when external motion impacts it. To facilitate sensing, the motion sensor can be turned "on," requiring current drain, and the output can then be sampled to generate an output. Keeping the motion sensor "on" all the time may drain battery sourced current unnecessarily, and so duty cycling is performed to minimize current draw in some embodiments.

Processing module 110 may be configured to direct the operation of LCP 100. For example, processing module 110 may be configured to receive cardiac electrical signals from electrical sensing module 106 and/or physiological signals from mechanical sensing module 108. Based on the received signals, processing module 110 may determine, for example, occurrences and types of arrhythmias. Processing module 110 may further receive information from communication module 102. In some embodiments, processing module 110 may additionally use such received information to determine occurrences and types of arrhythmias. However, in other embodiments, LCP 100 may use the received information instead of the signals received from electrical sensing module 106 and/or mechanical sensing module 108—for instance if the received information is deemed to be more accurate than the signals received from electrical sensing module 106 and/or mechanical sensing module 108 or if electrical sensing module 106 and/or mechanical sensing module 108 have been disabled or omitted from LCP 100.

After determining therapy is needed, processing module 110 may control pulse generator module 104 to generate electrical stimulation pulses in accordance with one or more electrical stimulation therapy regimens. For example, processing module 110 may control pulse generator module 104 to generate pacing pulses with varying parameters and in different sequences to effectuate one or more electrical stimulation therapies. As one example, in controlling pulse generator module 104 to deliver bradycardia pacing therapy, processing module 110 may control pulse generator module 104 to deliver pacing pulses designed to capture the heart of the patient at a regular interval to help prevent the heart of a patient from falling below a predetermined threshold.

In some embodiments, processing module 110 may further control communication module 102 to send information to other devices. For example, processing module 110 may control communication module 102 to generate one or more communication signals for communicating with other devices of a system of devices. For instance, processing module 110 may control communication module 102 to generate communication signals in particular pulse sequences, where the specific sequences convey different information. Communication module 102 may also receive communication signals for potential action by processing module 110.

In some embodiments, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby potentially increasing the battery life of LCP 100. In other instances, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip.

Processing module 110, in additional embodiments, may include a memory circuit and processing module 110 may store information on and read information from the memory circuit. In other embodiments, LCP 100 may include a separate memory circuit (not shown) that is in communication with processing module 110, such that processing module 110 may read and write information to and from the separate memory circuit. The memory circuit, whether part of processing module 110 or separate from processing module 110, may be volatile memory, non-volatile memory, or a combination of volatile memory and non-volatile memory.

Energy storage module 112 may provide a power source to LCP 100 for its operations. In some embodiments, energy storage module 112 may be a non-rechargeable lithium-based battery. In other embodiments, the non-rechargeable battery may be made from other suitable materials. In some embodiments, energy storage module 112 may include a rechargeable battery. For embodiments with a rechargeable battery, there may additionally be a recharging circuit using, for example, a coil that receives an electrical or magnetic field to facilitate recharging transcutaneously, as is well known in the art. In other embodiments, biological energy capture devices may be used to take advantage of energy that can be generated using the cardiac or other biological motion. In still other embodiments, energy storage module 112 may include other types of energy storage devices such as super capacitors.

Collectively the processing module 110, mechanical sensing module 108, electrical sensing module 106, pulse generator module 104, and communication module 102 may be referred to as the operational circuitry of the LCP. In some examples the individual modules 102, 104, 106, 108, 110 may be subcomponents on a single hybrid or circuit board, or even within a single VSLI or ASIC, or may be spread across several hybrids, circuit boards, VSLI or ASIC components. In some examples, certain elements of processing module 110 are performed in the digital domain—such as determining whether to deliver therapy and operating the communication module when awoken for such a purpose—while others are performed in the analog domain—such as ongoing monitoring of the received electrical and/or motion signal until a significant perturbation of either signal or a timeout occurs, allowing the digital circuitry to stay in a low power state by duty cycling to sleep. On whole, the operational circuitry may be configured to perform the various methods shown herein and below claimed, by reference to memory and/or by operation of application-specific circuitry and/or ASIC chips.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. The one or more anchors 116 are shown schematically in FIG. 1. The one or more anchors 116 may include any number of fixation or anchoring mechanisms. For example, one or more anchors 116 may include one or more pins, staples, threads, screws, helix, tines, and/or the like. In some embodiments, although not shown, one or more anchors 116 may include threads on its external surface that may run along at least a partial length of an anchor member. The threads may provide friction between the cardiac tissue and the anchor to help fix the anchor member within the cardiac tissue. In some cases, the one or more anchors 116 may include an anchor member that has a cork-screw shape that can be screwed into the cardiac tissue. In other embodiments, anchor 116 may include other structures such as barbs, spikes, or the like to facilitate engagement with the surrounding cardiac tissue.

In some examples, LCP 100 may be configured to be implanted on a patient's heart or within a chamber of the patient's heart. For instance, LCP 100 may be implanted within any of a left atrium, right atrium, left ventricle, or right ventricle of a patient's heart. By being implanted within a specific chamber, LCP 100 may be able to sense cardiac electrical signals originating or emanating from the specific chamber that other devices may not be able to sense with such resolution. Where LCP 100 is configured to be implanted on a patient's heart, LCP 100 may be configured to be implanted on or adjacent to one of the chambers of the heart, or on or adjacent to a path along which intrinsically generated cardiac electrical signals generally follow. In these examples, LCP 100 may also have an enhanced ability to sense localized intrinsic cardiac electrical signals and deliver localized electrical stimulation therapy.

In some instances, LCP 100 may be configured to deliver rate-adaptive pacing therapy to a patient's heart. For instance, LCP 100 may be configured to deliver electrical stimulation pulses to the heart of the patient on an on-going basis to help ensure that the patient's heart contracts in a safe and effective manner. LCP 100 may additionally sense one or more signals, for example using electrical sensing module 106 and/or mechanical sensing module 108, and determine, based on the sensed one or more signals, whether to change the rate of delivery of the electrical stimulation pulses.

For example, based on the sensed one or more signals, LCP 100 may determine that there is less of a need for cardiac output, and may decrease the rate of delivery of the electrical stimulation pulses. In other instances, based on the one or more sensed signals, LCP 100 may determine that there is a need for increased cardiac output, and may increase the rate of delivery of the electrical stimulation pulses. Adjusting the rate of delivery of the electrical stimulation pulses based on the sensed one or more signals may extend the battery life of LCP 100 by only requiring higher rates of delivery of electrical stimulation pulses when the sensed one or more signals indicate there is a need for increased cardiac output. Additionally, adjusting the rate of delivery of the electrical stimulation pulses may increase a comfort level of the patient by more closely matching the rate of delivery of electrical stimulation pulses with the cardiac output need of the patient.

Where LCP 100 adjusts the rate of delivery of electrical stimulation pulses based on the sensed one or more signals, LCP 100 may in some cases determine a respiration rate based on the sensed one or more signals. Respiration rate may be indicative of a relative cardiac output need for the patient. For example, an increased respiration rate may indicate that there is a need for increased cardiac output, and a decreased respiration rate may indicate less of a need for cardiac output. Accordingly, and when so provided, LCP 100 may adjust the rate of delivery of the electrical stimulation pulses based on the determined respiration rate.

In at least some examples, LCP 100 may include a motion sensor (such as an accelerometer) and may determine a measure related to the respiration rate based on the sensed motion sensor signal. Where LCP 100 is implanted on a patient's heart or within the heart, the motion sensor signal may include signals indicative of movement related to a number of different causes. For instance, the motion sensor signal may include movement related to the gross movement of the patient, such as walking, bending, or other gross body movements. Additionally, the motion sensor signal may include movement related to the contraction of the heart, particularly when LCP 100 is implanted on or within the heart. Additionally, the motion sensor signal may include movement related to the inhalation and exhalation of the patient (i.e. respiration). For instance, as a patient breathes in and out, the lungs apply different pressure to the heart and the intrathoracic pressure changes accordingly. This change in the intrathoracic pressure may cause changes in the shape and size of the various chambers of the heart, as well as the movement of the heart and the heart chambers. After inhalation, the intrathoracic pressure may be relatively higher, which may decrease the volume of blood that flows into one or more of the chambers of the heart during a cardiac cycle. Conversely, after exhalation, the intrathoracic pressure may be relatively lower, which may allow relatively more blood to enter the chambers of the heart during a cardiac cycle. These differences in the amount of blood flowing into and out of the heart and any movement of the heart or heart chambers due to the changes in intrathoracic pressure may be contained in the motion sensor signal.

Although an LCP serves as the platform for much of the below description and above detail, any implantable device having a motion sensor may take advantage of the presently described enhancements. Other devices may include drug or other substance delivery systems, neurostimulator or neuromodulation systems, and implantable cardiac monitoring systems, for example.

Figure 2:
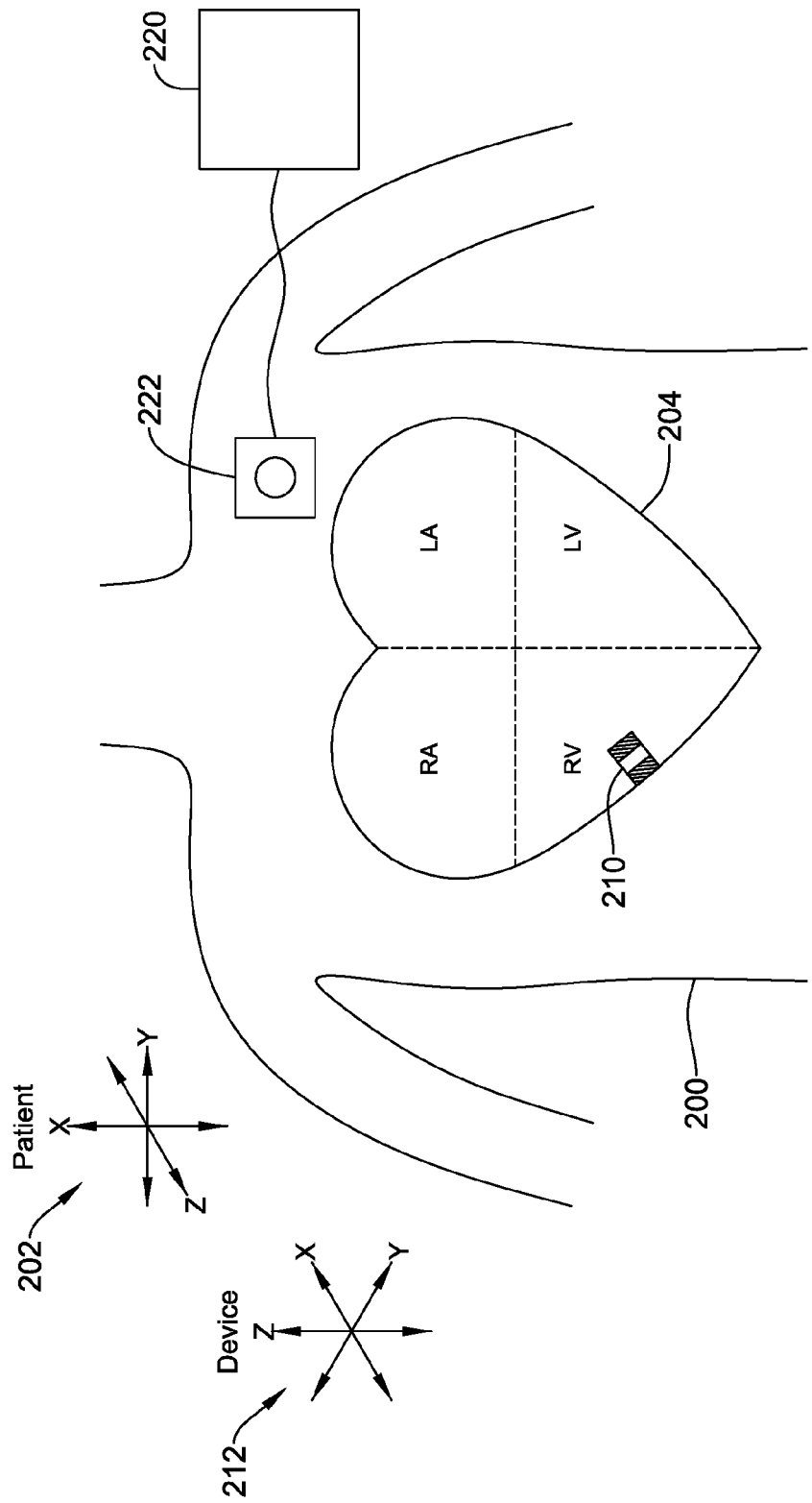
FIG. 2 shows an illustrative example of a system implanted in a patient.

FIG. 2 shows an illustrative example of a system implanted in a patient. The patient 200 is shown upright, having a patient frame of reference highlighted at 202. The patient has an implantable device 210 in the heart 204. The implantable device is shown as a leadless cardiac pacemaker (LCP), and may take the form generally shown and described above. Alternatively, the implantable device 210 may be provided as an implantable recorder such as an implantable loop recorder or subcutaneous cardiac monitor. The implantable device 210 may instead be a neurostimulation apparatus for implantation in the brain, near the spine or in any other location where therapy may be useful. Although an LCP serves as the platform for much of the below description and above detail, any implantable device having a motion sensor may take advantage of the presently described enhancements.

The implantable system also includes a programmer 220 having (optionally) a programming head 222 for placement on the patient. For an LCP, and some other implantable devices, some configurations may use what is referred to as conducted communication within the patient tissue, which can be read by a programming head 222 placed on the patient. For other configurations, and/or for other devices, inductive or RF telemetry may be performed, with or without the programming head 222 on the patient.

The implantable device 210 is shown in the right ventricle of the heart 204. As described above, the implantable device 210 includes a motion sensor. Such motion sensors may have several axes along which motion may be detected; typically there are three axes or dimensions. Because the exact position of the device 210 will vary for a given patient 200 based on the cardiac condition and implantation method for such a product, it is entirely likely that the frame of reference for the implanted device 210 will be different from the frame of reference for the patient. Thus, the patient has a frame of reference defined by axes Xp, Yp, and Zp, shown at 202, while the device has a frame of reference defined by axes Xd, Yd, and Zd.

To facilitate ease of understanding for the physician of patient activity and/or position during a time of interest, the present inventors have recognized it would be useful for the device 210 to store a configuration of the motion sensor output that normalizes every such device for later interrogation. Thus a conversion matrix can be calculated for a particular patient 200 having a particular device, and the conversion matrix would be stored by the implant device 210 for later use during a programming session. Thus the output of a three dimensional motion sensor can be converted from the frame of reference 212 of the implantable device to the frame of reference 202 of the patient by storing the matrix:

| $a_{11}$ | $a_{12}$ | $a_{13}$ |
| --- | --- | --- |
| $a_{21}$ | $a_{22}$ | $a_{23}$ |
| $a_{31}$ | $a_{32}$ | $a_{33}$ |

The conversion from device axes Xd, Yd, and Zd to standardized or patient axes Xp, Yp, and Zp can occur according to these formulas:

$Xp = a11*Xd + a12*Yd + a13*Zd$ $Yp = a21*Xd + a22*Yd + a23*Zd$ $Zp = a31*Xd + a32*Yd + a33*Zd$

The matrix can be calculated by observing the output of the motion sensor as the patient assumes a variety of different postures; preferably at least two postures would be used to eliminate ambiguity; three or more postures may be used. To generate the matrix, it may be helpful to capture and average samples across a relatively long period of time—possibly several samples equally spaced across several cardiac cycles—to reduce the impact of the motion of the heart during the cardiac cycle, since such additional movement would show up as noise in the calculation. Such issues may arise more in a device residing entirely in the heart as opposed to devices, such as implantable loop recorders or patient monitors, or traditional pacemakers, that do not place the accelerometer in contact with the myocardium itself.

Storing the conversion matrix in the implantable device for later recall would allow any programmer, possessed by any physician, to determine what sort of activity or posture the patient had ongoing at the time of an event of interest. For example, if the patient suffers a syncopal episode, knowing the patient posture just before the episode may be helpful in determining what exactly happened. In another example, if a patient having an implantable device receives an inappropriate therapy, understanding the patient posture may aid in troubleshooting any difficulties with sensing that result from changing postures.

In another example, a patient does not receive inappropriate therapy, but an implantable device determines that malsensing occurred. Malsensing may be determined by, for example, determining that double detection, or other overdetection, or noise, has been identified. Troubleshooting such an event can be very difficult because the patient would be unaware of malsensing if no therapy is delivered. If malsensing is identified, however, the implantable device can call a function which records the output of the motion sensor at the time of malsensing. Using a normalized frame of reference, the physician may better be able to determine a root cause for malsensing. In one example, a subcutaneous implantable defibrillator, such as the S-ICD System™, from Cameron Health, Inc. and Boston Scientific Corporation, is used in conjunction with a leadless cardiac pacemaker as in FIGS. 1-2, and if malsensing is identified by the subcutaneous implantable defibrillator (due to oversensing or noise), the subcutaneous implantable defibrillator requests that the leadless cardiac pacemaker record and/or transmit to the subcutaneous implantable defibrillator patient position or motion data at the time of the malsensing.

Figure 3:
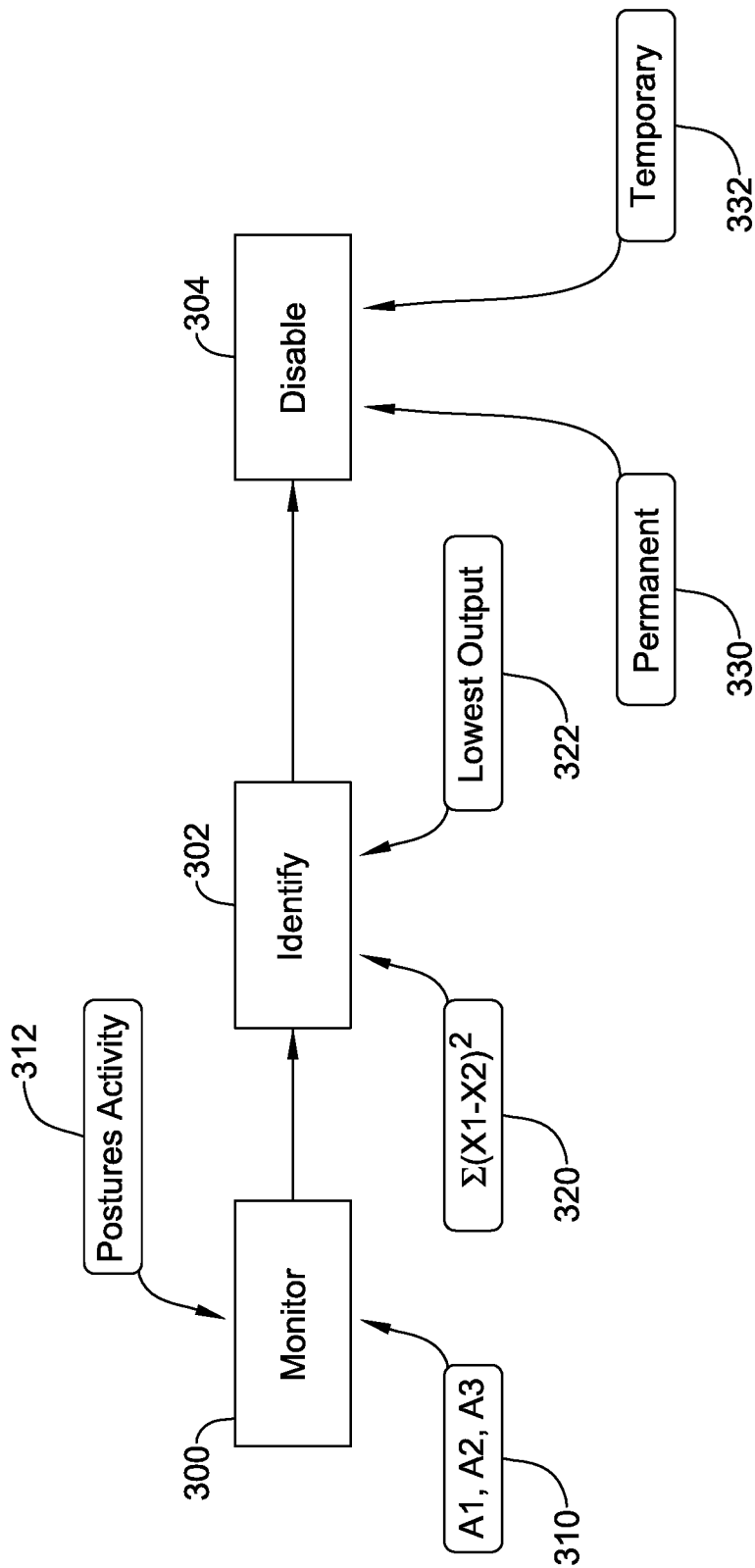
FIGS. 3-5 are flow diagrams for illustrative methods.
Figure 4:
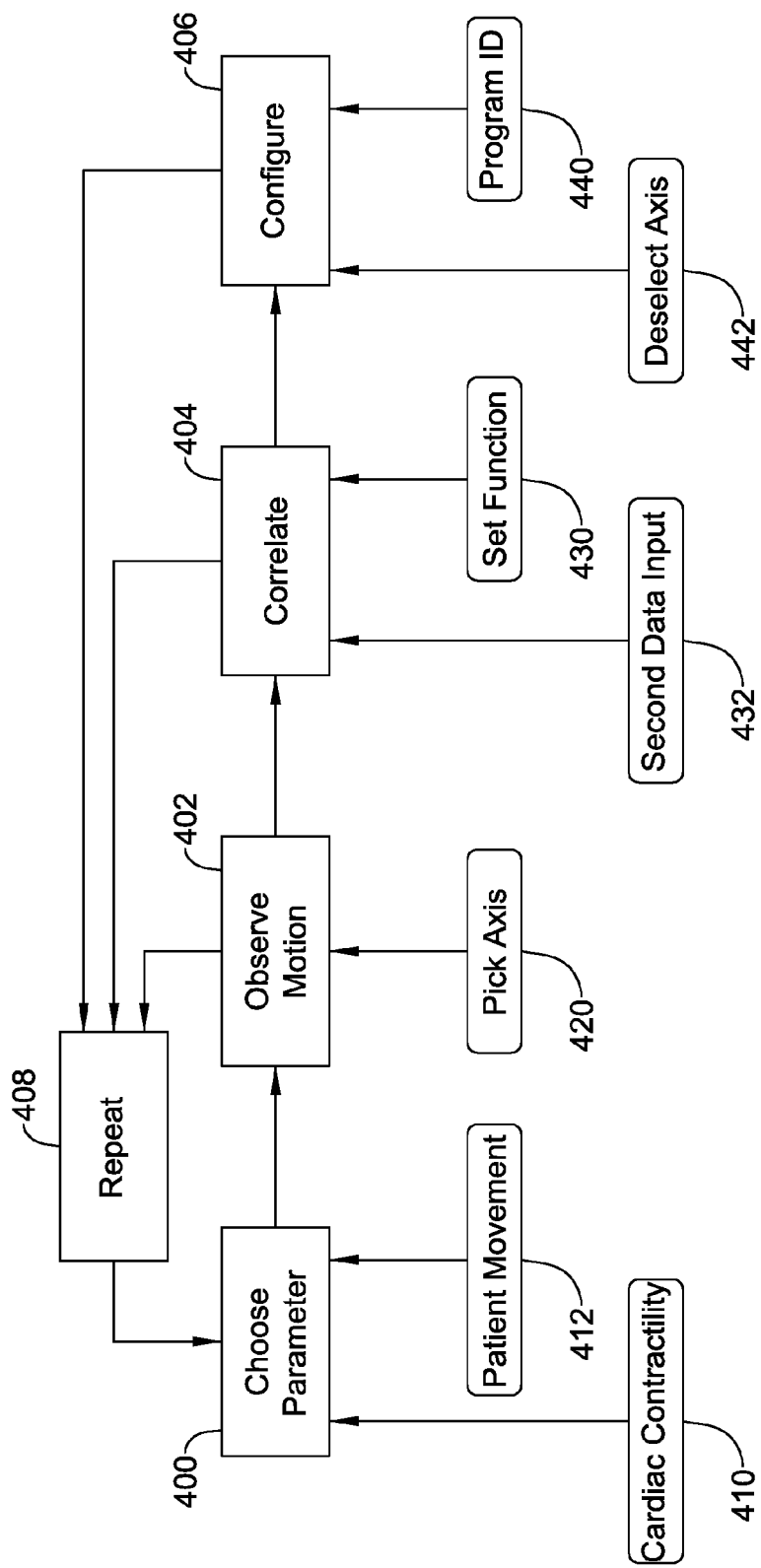
Figure 5:
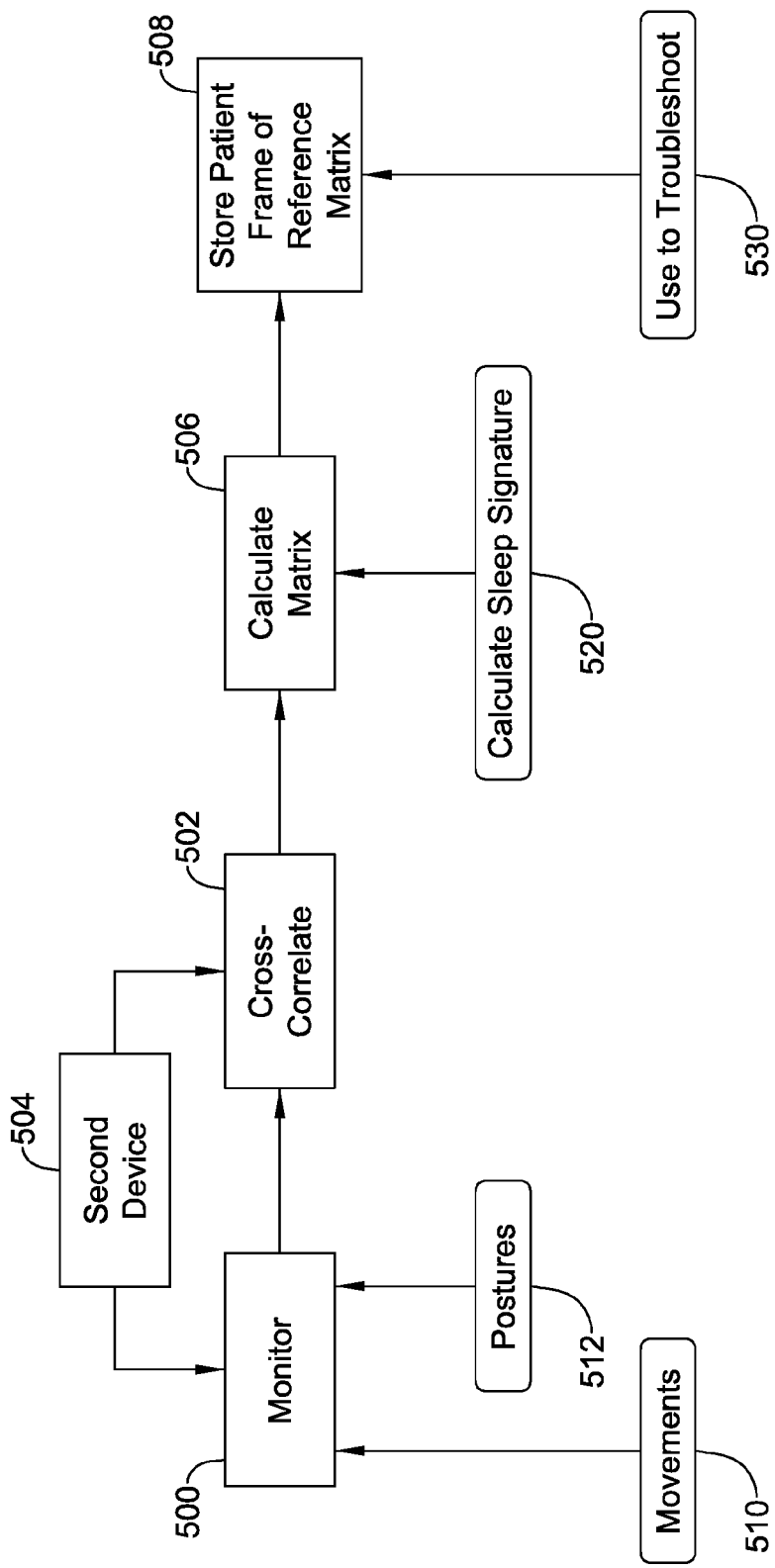

FIGS. 3-5 are flow diagrams for illustrative methods. FIG. 3 illustrates a method for reducing power consumption in an implantable device. At block 300, the output of a motion sensor is monitored. The motion sensor may have multiple axes and separate outputs for each axis. Next, a least used or useful output of the motion sensor is identified at 302. That least useful output is disabled at 304. The monitoring, as noted, may include multiple axes such as axis A1, A2 and A3, as noted at 310. Monitoring 300 may occur in a controlled or ambulatory setting, and may include monitoring for multiple postures or activity, as indicated at 312.

In a controlled setting, for example, the patient may be asked in clinic to assume a plurality of postures or perform selected activities. Illustrative postures may include sitting, standing, prone, lying on the back, recumbent, lying on the side (left/right), or any particular posture of interest for a given patient such as the posture the patient usually sleeps in. Illustrative physical activities that may be requested include walking, standing up or sitting down, rolling over, jogging or running, or an activity that the person engages in frequently such as a favorite exercise (elliptical machine, swimming, golf swing), or a work activity that is performed often (a mechanic emulating the movement to get under a vehicle, or a desk worker sitting at a desk and typing).

The identification of a least useful vector at 302 may be performed by monitoring for the lowest output axis of those enabled by the motion sensor. More complex analysis may be done by observing the change over time, for example, summing the sample-to-sample differences (or squares thereof) as noted at 320. Sum of differences may be performed by observing outputs while in different postures or during active movement, rather than on a sample to sample basis. For example, an axis that show significant motion from sample to sample, but which does not provide a significant difference from one posture to another, or between outputs while the patient is at rest and active, may not be helpful in identifying patient movement or activity. The aim is to identify any axis which fails to provide useful data. Sometimes this will be indicated by an axis that provides only small signals.

After activities and/or postures are assessed, a temporary 332 or (semi) permanent 330 disabling of one or more axes may be performed. For "permanent" 330 disabling of an axis in the controlled or clinical setting, the analysis may be performed again in a subsequent programming session at a subsequent clinic visit. In some examples, if a malsensing or dangerous condition is identified by an implantable device, all axes of the implantable device motion sensor may be re-enabled to allow data capture associated with the malsensing or dangerous condition.

In an ambulatory setting, it may be useful to perform this process periodically or as changes are identified. For example, monitoring may be performed for 2 to 10 seconds and identification 302 and temporary disabling 304/332 may be performed. In this context, if the heart rate changes, or the remaining, selected axes show significant changes, the temporary disabling of one or more axes may be undone. Alternatively, if temporary 332 disabling of an axis is done, then after a set period of time, for example, one to thirty minutes (or more or less), the process restarts at block 300.

In one example, data from one or more axis of an accelerometer may be ignored or turned off by the implantable system. As noted above, in use when an accelerometer output is taken, this may yield a plurality of outputs that can be run through a matrix of coefficients to obtain a measure of patient movement. To normalize the output of the accelerometer the corresponding matrix coefficients for those axes which are not deselected may be updated.

FIG. 4 shows another illustrative example. Here, the particular axes of a motion sensor are to be correlated with particular physiological parameters. In an example, a parameter is selected for analysis at 400. Motion sensor output is observed at 402, and the parameter and the motion sensor outputs are correlated at 404. Once one or more axes are correlated to—or shown to be uncorrelated to—the selected parameter, a configuration is stored at 406. The process may be repeated at 408 for multiple parameters or to analyze individual axes or combinations of axis within block 402.

For example, a parameter such as cardiac contractility 410 can be selected at block 400. Motion sensor outputs are observed at 402, including selecting single or multiple axes at 420. The correlation of the parameter to the selected axes may be performed by comparing the observed motion 402 to a second data input 432. The second data input 432 for correlation 404 with cardiac contractility may be, for example, a cardiac electrogram or surface electrocardiogram, an imaging system, or a blood pressure monitor output, any of which will indicate when the cardiac muscle is in motion as myocardial contractions occur or blood pressure/flow rises and drops during the cardiac cycle. This correlation 404 can be used to show that one or more axes are not useful in monitoring the selected parameter, leading to deselection of an axis 442 as part of the configuration 406. Correlation 404 may include setting a function 420 and relevant thresholds for storage during configuration step 406. The configuration step 406 may also include programming the implantable device to deselect an axis and/or to store the function calculated at 430.

In another example, the chosen parameter may be patient movement 412. Again the motion sensor outputs may be monitored at 402 by selecting and deselecting combinations of the axes of the motion sensor. Correlation is again performed at 404. Here the second data input for patient motion monitoring may come from an associated programmer, which would be used in a clinical setting to allow the user to indicate to the implanted device whether the patient is moving or not. Again the correlation 404 facilitates identification of the function 430 for analysis of the output (for example, setting threshold to determine whether the patient is active). The correlation 404 may also allow identification of one or more axes of the motion sensor that do not provide useful information for the function 430. Again, the configuring step 406 may store data indicating which axis to deselect 442, if any, and to program the implantable device 440 to accurately use the motion sensor output.

FIG. 5 shows another illustrative example. Here monitoring is performed at block 500 and cross correlation is performed at 502 against the outputs or other information provided by a second device 504. Next a matrix is calculated at 506, and a patient frame of reference matrix is stored in the implantable device at 508. Monitoring 500 may be performed while the patient is moving 510 or in various postures 512.

The second device 504 may be a programmer used to indicate which movements 510 or postures 512 the patient is engaged in or has assumed. The second device 504 may instead be a wearable accelerometer or motion sensor for the patient. In another example, the second device 504 may be a second implantable medical device such as a pacemaker, defibrillator, neuromodulation device, etc.

In a specific example, a sleep signature for the patient may be calculated, as noted at 520. This may be performed as part of a sleep study for the patient, where the device engages in a specific mode of repeated monitoring 500 over the course of a night to gather data allowing the motion sensor output to be repeatedly visited. Once a patient sleep signature 520 is generated, the implantable device may be able to positively determine that the patient is likely asleep. Such a determination can be used to disable rate adaptive pacing during the night for the patient, to reduce power consumed by analytics directed at rate adaptive pacing.

As discussed briefly above, the patient frame of reference matrix may be used in troubleshooting 530. For example, sometimes events are detected by an implantable device such as a long pause, an arrhythmia such as a tachycardia, or excess noise. Any of these conditions, when identified by an implantable device, may be used to trigger data capture with the motion sensor to determine whether there is a postural or activity-related element to the anomaly.

In several of the above examples, significant data calculations are performed. To simplify implant device programming and electronics, or to reduce power usage in making complex calculations, data analysis may be performed by the external programmer after motion sensor outputs are telemetered out to the programmer. Alternatively, the implant device may perform its own data analysis.

A first non-limiting example takes the form of an implantable medical device comprising: a power source; a plurality of electrodes for use in one or more of biological signal monitoring or providing a electrical therapy; a motion sensor having at least first and second axes of sensitivity; and operational circuitry configured to control the use of the electrodes and motion sensor for one or more of capturing biological signal data and patient motion and providing electrical therapy; wherein the operational circuitry is configured to perform the following: monitoring an output from a motion sensor along at least first and second axes; identifying one of the first and second axes as providing less information than one or more other axes; and at least temporarily disabling the identified axis of the motion sensor.

A second non-limiting example takes the form of a device as in the first non-limiting example, wherein the operational circuitry is further configured such that the at least temporarily disabling step comprises disabling the identified axis for a predetermined period of time, and the operational circuitry is further configured to perform the following: re-enabling the temporarily disabled axis; and repeating the steps of monitoring, identifying and at least temporarily disabling steps.

A third non-limiting example takes the form of a device as in either of the first or second non-limiting examples, wherein the operational circuitry is further configured to perform the following: while the identified axis is disabled, monitoring the output of the motion sensor on one or more remaining axes; observing a change in output of the one or more remaining axes; and re-enabling the identified axis. A fourth non-limiting example takes the form of a device as in any of the first to third non-limiting examples, wherein the operational circuitry is further configured to use an output of the motion sensor from at least one axis which is not at least temporarily disabled to monitor activity of the patient. A fifth non-limiting example takes the form of a device as in any of the first four non-limiting examples, wherein the implantable medical device is configured as a leadless cardiac pacemaker for placement entirely inside the heart of a patient, wherein the operational circuitry is further configured to apply an algorithm for rate responsive pacing to determine a pacing rate for delivery of pacing pulses, and to deliver rate responsive pacing therapy to the patient using at least an output from the motion sensor.

A sixth non-limiting example takes the form of a device as in any of the first to fifth non-limiting examples, wherein the operational circuitry is configured to determine and store a conversion matrix for normalizing an output of the motion sensor to a patient frame of reference. A seventh non-limiting example takes the form of a device as in any of the first to sixth non-limiting examples, wherein the motion sensor has three axes.

An eighth non-limiting example takes the form of a method of initializing a device as in any of the first to seventh non-limiting examples, the method comprising: instructing a patient to perform a first activity with the implantable device implanted; instructing the implantable device to assess motion sensor outputs; instructing the patient to perform a second activity with the implantable device implanted; and instructing the implantable device to further assess motion sensor outputs. A ninth non-limiting example takes the form of a method as in the eighth non-limiting example, wherein the first activity and second activities are each one of: assuming a posture selected from the group consisting of sitting, standing, supine, prone, or a sleep position; or engaging in physical activity.

A tenth non-limiting example takes the form of an implantable medical device comprising: a power source; a plurality of electrodes for use in one or more of biological signal monitoring or providing a electrical therapy; a motion sensor having at least first and second axes of sensitivity; and operational circuitry configured to control the use of the electrodes and motion sensor for one or more of capturing biological signal data and patient motion and providing electrical therapy; wherein the operational circuitry is configured to perform the following: capturing a plurality of outputs of the motion sensor for at least first and second axes of the motion sensor; establishing a standard frame of reference for the patient using the outputs of the motion sensor.

An eleventh non-limiting example takes the form of an implantable device system comprising: the implantable medical device of the tenth non-limiting example, and an external programmer configured to communicate with the implantable medical device, wherein the programmer and implantable medical device are configured to cooperate in the capturing step by the programmer instructing a patient to assume a series of postures.

A twelfth non-limiting example takes the form of a system as in the eleventh non-limiting example, further comprising a second medical device having a motion sensor, wherein the programmer is configured to receive motion sensor data from each of the implantable medical device and the second medical device to establish a conversion matrix for converting an output of the implantable medical device to a patient standard frame of reference.

A thirteenth non-limiting example takes the form of a device as in the tenth non-limiting example, wherein the motion sensor has three axes. A fourteenth non-limiting example takes the form of a device as in either of the tenth or thirteenth non-limiting examples, wherein the implantable medical device is an implantable leadless cardiac pacemaker. A fifteenth non-limiting example takes the form of a device as in any of the tenth, thirteenth, or fourteenth non-limiting examples, wherein the operational circuitry is configured to determine that malsensing has occurred and record an output of the motion sensor in response to the malsensing.

A sixteenth non-limiting example takes the form of a method of operation in an implantable device, the implantable device comprising a motion sensor, the method comprising: monitoring an output from a motion sensor along at least first and second axes; identifying one of the first and second axes as providing less information than one or more other axes; and at least temporarily disabling the identified axis of the motion sensor.

A seventeenth non-limiting example takes the form of a method as in the sixteenth non-limiting example, wherein the implantable device is a leadless pacemaker configured for implantation within the heart of a patient. An eighteenth non-limiting example takes the form of a method as in either of the sixteenth or seventeenth non-limiting examples, wherein the motion sensor has three axes. A nineteenth non-limiting example takes the form of a method as in any of the sixteenth to eighteenth non-limiting examples, wherein the at least temporarily disabling step comprises disabling the identified axis for a predetermined period of time and the method comprises: re-enabling the temporarily disabled axis; and repeating the steps of monitoring, identifying and at least temporarily disabling steps.

A twentieth non-limiting example takes the form of a method as in any of the sixteenth to nineteenth non-limiting examples, further comprising: while the identified axis is disabled, monitoring the output of the motion sensor on one or more remaining axes; observing a change in output of the one or more remaining axes; and re-enabling the identified axis. A twenty-first non-limiting example takes the form of a method as in any of the sixteenth to twentieth non-limiting examples, further comprising using an output of the motion sensor from at least one axis which is not at least temporarily disabled to monitor activity of the patient. A twenty-second non-limiting example takes the form of a method as in the twenty-first non-limiting example further comprising applying an algorithm for rate responsive pacing to determine a pacing rate for delivery of pacing pulses to the patient using at least an output from the motion sensor, and delivering the rate responsive pacing to the patient. A twenty-third non-limiting example takes the form of a method as in the twenty-first non-limiting example, further comprising normalizing an output of the motion sensor to a patient frame of reference.

A twenty-fourth non-limiting example takes the form of a method of initializing an implantable device having a motion sensor comprising: instructing a patient to perform a first activity; performing the method of claim 16 to assess motion sensor outputs; instructing a patient to perform a second activity; and repeating the method of claim 16 to further assess motion sensor outputs. A twenty-fifth non-limiting example takes the form of a method as in the twenty-fourth non-limiting example, wherein the first activity and second activities are each one of: assuming a posture selected from the group consisting of sitting, standing, supine, prone, or a sleep position; or engaging in physical activity.

A twenty-sixth non-limiting example takes the form of a method of operation in an implantable device configured for placement inside the heart of a patient, the implantable device comprising a motion sensor, the method comprising: selecting a first parameter; observing at least first and second outputs of the motion sensor, the first and second outputs relating to respective first and second axes of measurement for the motion sensor; correlating at least one of the at least first and second outputs, or a combination thereof, to the first parameter; storing a first configuration of the at least first and second outputs of the motion detector corresponding to the first parameter; applying the first configuration to outputs of the motion sensor to monitor characteristics of the first parameter.

A twenty-seventh non-limiting example takes the form of a method as in the twenty-sixth non-limiting example, further comprising selecting a second parameter and repeating the observing, and correlating steps, and then: storing a second configuration of the at least first and second outputs of the motion detector corresponding to the second parameter; applying the second configuration to outputs of the motion sensor to monitor characteristics of the second parameter. A twenty-eighth non-limiting example takes the form of a method as in the twenty-seventh non-limiting example, wherein the first parameter is cardiac contractility, and the second parameter is patient motion; further comprising: using the first configuration to monitor the cardiac contractility of the patient and generate diagnostic data therefrom for use by a physician; and using the second configuration to monitor the activity level of the patient and facilitate a rate responsive pacing output regimen for the patient. A twenty-ninth non-limiting example takes the form of a method as in the twenty-eighth non-limiting example, further comprising the implantable device delivering the rate responsive pacing output regimen to the patient.

A thirtieth non-limiting example takes the form of a method as in the twenty-sixth non-limiting example, wherein the first parameter is patient motion and the method further comprises: delivering pacing therapy to the patient via the implantable medical device; and using the first configuration to facilitate a rate responsive pacing output regimen for the patient in which the rate at which pacing therapy is delivered adjusts in view of patient activity. A thirty-first non-limiting example takes the form of a method as in the twenty-sixth non-limiting example, wherein the implantable device includes a sensing circuit for sensing cardiac electrical signals of the patient, and the method further comprises: using a sensed cardiac electrical signal, determining that a cardiac event took place; using the stored configuration, analyzing one or more outputs from the motion sensor to determine a state of the parameter during the cardiac event.

A thirty-second non-limiting example takes the form of a method of operation in an implantable device configured for placement inside the heart of a patient, the implantable device comprising a motion sensor, the method comprising: capturing a plurality of outputs of the motion sensor for at least first and second axes of the motion sensor; establishing a standard frame of reference for the patient using the outputs of the motion sensor.

A thirty-third non-limiting example takes the form of a method as in the thirty-second non-limiting example, wherein the capturing step is performed by having the patient assume a series of postures. A thirty-fourth non-limiting example takes the form of a method as in the thirty-third non-limiting example, further comprising capturing an output of a second device while the patient assumes the series of postures, wherein the step of establishing a standard frame of reference is performed by comparing an output from the second device to the captured plurality of outputs of the motion sensor. A thirty-fifth non-limiting example takes the form of a method as in either of the thirty-third or thirty-fourth non-limiting example, wherein the step of having the patient assume a series of postures is performed by having a programmer provide an instruction for the patient and await an indication that the patient has complied.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of operation in an implantable device configured for placement inside the heart of a patient, the implantable device comprising a motion sensor, the method comprising:
    selecting a first parameter;
    observing at least first and second outputs of the motion sensor, the first and second outputs relating to respective first and second axes of measurement for the motion sensor;
    correlating at least one of the at least first and second outputs, or a combination thereof, to the first parameter;
    storing a first configuration of the at least first and second outputs of the motion detector for measuring the first parameter;
    applying the first configuration to outputs of the motion sensor to monitor characteristics of the first parameter.

2. The method of claim 1 further comprising selecting a second parameter and repeating the observing, and correlating steps, and then:
    storing a second configuration of the at least first and second outputs of the motion detector corresponding to the second parameter;
    applying the second configuration to outputs of the motion sensor to monitor characteristics of the second parameter.

3. The method of claim 2 wherein the first parameter is cardiac contractility, and the second parameter is patient motion; further comprising:
    using the first configuration to monitor the cardiac contractility of the patient and generate diagnostic data therefrom for use by a physician; and
    using the second configuration to monitor the activity level of the patient and facilitate a rate responsive pacing output regimen for the patient.

4. The method of claim 3 further comprising the implantable device delivering the rate responsive pacing output regimen to the patient.

5. The method of claim 1 wherein the first parameter is patient motion and the method further comprises:
    delivering pacing therapy to the patient via the implantable medical device; and
    using the first configuration to facilitate a rate responsive pacing output regimen for the patient in which the rate at which pacing therapy is delivered adjusts in view of patient activity.

6. The method of claim 1 wherein the implantable device includes a sensing circuit for sensing cardiac electrical signals of the patient, and the method further comprises:
    using a sensed cardiac electrical signal, determining that a cardiac event took place;
    using the stored configuration, analyzing one or more outputs from the motion sensor to determine a state of the parameter during the cardiac event.

7. The implantable medical device of claim 1 wherein:
    the operational circuitry is configured to select a second parameter, observe the at least first and second outputs of the motion sensor, and correlate at least one of the at least first and second outputs, or a combination thereof, to the second parameter, and then:
    store a second configuration of the at least first and second outputs of the motion detector corresponding to the second parameter, and apply the second configuration to outputs of the motion sensor to monitor characteristics of the second parameter.

8. The implantable medical device of claim 7 wherein:
the first parameter is cardiac contractility, and the second parameter is patient motion;
the operational circuitry is configured to use the first configuration to monitor the cardiac contractility of the patient and generate diagnostic data therefrom for use by a physician; and
the operational circuitry is configured to use the second configuration to monitor the activity level of the patient and facilitate a rate responsive pacing output regimen for the patient.

9. The implantable medical device of claim 8 wherein the operational circuitry is configured to deliver the rate responsive pacing output regimen to the patient using the electrodes.

10. The method of claim 1 further comprising obtaining a data input from a source other than the motion sensor in order to establish the correlation, and the first configuration defines a relationship, established using the second data input, between the outputs of the motion sensor and the first parameter, wherein the first parameter is cardiac contractility and the data input comprises information from one of a cardiac electrogram, a surface electrocardiogram, an imaging system, or a blood pressure monitor.

11. The method of claim 1 further comprising obtaining a data input from a source other than the motion sensor in order to establish the correlation, and the first configuration defines a relationship, established using the second data input, between the outputs of the motion sensor and the first parameter, wherein the first parameter is patient movement, and the data input is obtained from a programmer adapted to communicate with the implantable medical device, wherein the data input is an indication from the programmer whether the patient is moving or not.

12. An implantable medical device comprising:
a power source;
a plurality of electrodes for use in one or more of biological signal monitoring or providing an electrical therapy;
a motion sensor having at least first and second axes of sensitivity; and
operational circuitry configured to control the use of the electrodes and motion sensor for one or more of: capturing biological signal data, capturing patient motion data, and/or providing electrical therapy;
wherein:
the operational circuitry is configured to select a first parameter;
the operational circuitry is configured to observe at least first and second outputs of the motion sensor, the first and second outputs relating to respective first and second axes of measurement for the motion sensor;
the operational circuitry is configured to correlate at least one of the at least first and second outputs, or a combination thereof, to the first parameter;
the operational circuitry is configured to store a first configuration of the at least first and second outputs of the motion detector for measuring the first parameter; and
the operational circuitry is configured to apply the first configuration to outputs of the motion sensor to monitor characteristics of the first parameter.

13. The implantable medical device of claim 12 wherein:
the first parameter is patient motion;
the operational circuitry is configured to deliver pacing therapy to the patient using the electrodes; and
the operational circuitry is configured to use the first configuration to facilitate a rate responsive pacing output regimen for the patient in which the rate at which pacing therapy is delivered adjusts in view of patient activity.

14. The implantable medical device of claim 12 wherein:
the operational circuitry is configured to use signals from the electrodes for sensing cardiac electrical signals of the patient;
the operational circuitry is configured to use a sensed cardiac electrical signal to determine that a cardiac event took place; and
the operational circuitry is configured to use the stored configuration to analyze one or more outputs from the motion sensor to determine a state of the parameter during the cardiac event.

15. An implantable leadless cardiac pacemaker taking the form of an implantable medical device as in claim 12.

16. An implantable cardiac monitor taking the form of an implantable medical device as in claim 12.

17. An implantable neuromodulation device taking the form of an implantable medical device as in claim 12.

18. The implantable medical device of claim 12 wherein the operational circuitry is configured to obtain a data input from a source other than the motion sensor in order to establish the correlation, and the first configuration defines a relationship, established using the data input, between the outputs of the motion sensor and the first parameter, wherein the first parameter is cardiac contractility and the data input comprises information from one of a cardiac electrogram, a surface electrocardiogram, an imaging system, or a blood pressure monitor.

19. The implantable medical device of claim 12 wherein the operational circuitry is configured to obtain a data input from a source other than the motion sensor in order to establish the correlation, and the first configuration defines a relationship, established using the data input, between the outputs of the motion sensor and the first parameter, wherein the first parameter is patient movement, and the data input is obtained from a programmer adapted to communicate with the implantable medical device, wherein the data input is an indication from the programmer whether the patient is moving or not.

* * * * *